United States Patent [19]
Blevins et al.

[11] 3,982,420
[45] Sept. 28, 1976

[54] METHOD AND APPARATUS FOR DETERMINING THE PASTING TEMPERATURE OF STARCH AND THE LIKE

[75] Inventors: Charles W. Blevins, North Little Rock, Ark.; Thomas F. Protzman, Decatur, Ill.

[73] Assignee: A. E. Staley Manufacturing Company, Decatur, Ill.

[22] Filed: Jan. 20, 1975

[21] Appl. No.: 542,323

[52] U.S. Cl. .............................. 73/17 R; 73/64.1
[51] Int. Cl.² ................... G01N 25/02; G01N 33/10
[58] Field of Search ....... 73/17 R, 53, 61 R, 61.1 R, 73/64.1; 250/573; 356/208

[56] References Cited
UNITED STATES PATENTS

| | | | |
|---|---|---|---|
| 2,604,392 | 7/1952 | Brown | 73/53 |
| 3,008,324 | 11/1961 | Rayford | 73/17 |
| 3,173,288 | 3/1965 | Davis et al. | 73/17 |
| 3,173,289 | 3/1965 | Davis | 73/17 |
| 3,187,557 | 6/1965 | Holbourne | 73/17 |
| 3,545,254 | 12/1970 | Chassagne | 73/17 |
| 3,807,865 | 4/1974 | Gordon et al. | 73/17 X |
| 3,844,159 | 10/1974 | Mizutani | 73/17 |
| 3,869,912 | 3/1975 | Horvath | 73/15 |

OTHER PUBLICATIONS

"Chemistry and Industry of Starch," edited by Kerr, 1950, Academic Press, pp. 143–147.

*Primary Examiner*—Herbert Goldstein
*Attorney, Agent, or Firm*—Fitch, Even, Tabin & Luedeka

[57] ABSTRACT

A method and apparatus for determining the pasting temperature of starch and the like is disclosed wherein a quantity of starch granules are mixed to form a slurry which is heated while a light source is passed through the slurry. Photosensor means detect the light transmittance through the slurry and are connected in circuit to place a visual temperature display means in a hold condition displaying a temperature representative of the pasting temperature of the starch when the light transmittance reaches a predetermined threshold.

4 Claims, 4 Drawing Figures

METHOD AND APPARATUS FOR DETERMINING THE PASTING TEMPERATURE OF STARCH AND THE LIKE

The present invention relates generally to a method and apparatus for determining pasting temperatures, and more particularly, to a novel method and apparatus for determining the pasting temperature of starch and the like.

The pasting temperature of starch is defined generally as the temperature at which initial swelling of starch granules takes place when suspended in water. The pasting temperature of starch granules is an important characteristic in the processing of starch and starch products. If starch granules in suspension in water are heated, water penetrates the granules to hydrate them with resulting swelling. If the temperature of the starch suspension or slurry is heated above its pasting temperature, a viscous mass is produced and the starch granules lose their unique microscopic appearance or shape which may not be regained upon cooling to room temperature.

As starch granules are heated in water and caused to hydrate and swell, the refractive index of the granules approaches that of water, and the initially opaque slurry becomes more transparent. The present invention makes use of this characteristic of starch granules when heated in water to provide a novel method and apparatus for determining the pasting temperature of starch and the like.

The apparatus in accordance with the present invention greatly enhances and facilitates in-process control by rapidly determining the pasting temperature of starch without the need for elaborate sample preparation or skilled technicians. The method and apparatus in accordance with the present invention may be employed to determine the pasting temperature of any granular starch, native or modified, which pastes at a temperature below the atmospheric boiling point.

In carrying out the present invention, a quantity of starch granules is added to a quantity of water in a sample container to form a starch slurry which preferably is continuously stirred. A light beam is passed through the starch slurry within the sample container and photosensor means are aligned with the light source to detect light passage through the starch slurry. The starch slurry within the container is heated and the temperature of the starch slurry is sensed by temperature sensing means such as a thermistor disposed within the starch slurry. The temperature responsive thermistor and the photosensor means are connected in circuit with a temperature display device, such as a digital display panel device or meter. If the digital display device indicates light transmittance at the time the starch is pasted, the display device reading will not change when it is connected to the temperature detection circuit unless the light is shut off or the light beam is blocked. This would not be a normal manner for operating the instrument. As the starch slurry begins initial swelling, the opague slurry becomes more transparent. When the starch slurry reaches its pasting temperature, a predetermined light intensity threshold is sensed and the temperature display meter is placed in a "hold" condition displaying a digital reading representative of the temperature of the starch slurry sample.

Accordingly, one of the primary objects of the present invention is to provide a novel method and apparatus for detecting the pasting temperature of starch and the like.

Another object of the present invention is to provide a method and apparatus for determining the pasting temperature of starch which employs a digital display means and associated control circuitry operative to display the pasting temperature of a starch sample in a rapid and convenient manner without laborious sample preparation and measurement.

Still another object of the present invention is to provide a novel method and apparatus for detecting the pasting temperature of starch and the like wherein photosensor means is employed to detect light transmittance through a starch slurry sample during heating of the sample, the photosensor means operating, through switching means, to place a digital display meter device in a hold condition when a predetermined threshold light transmittance is detected, the display device being capable of indicating the pasting temperature of the starch.

Further objects and advantages of the present invention, together with the organization and manner of operation thereof, will become apparent from the following detailed description of the invention when taken in conjunction with the accompanying drawings wherein like reference numerals designate like elements throughout the several views, and wherein.

Figure 1:
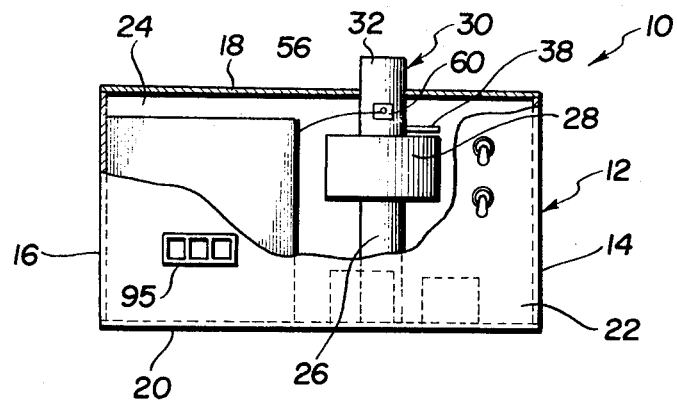
FIG. 1 is a front elevational view, partially broken away, of an apparatus for determining the pasting temperature of starch and the like in accordance with the present invention.
Figure 2:
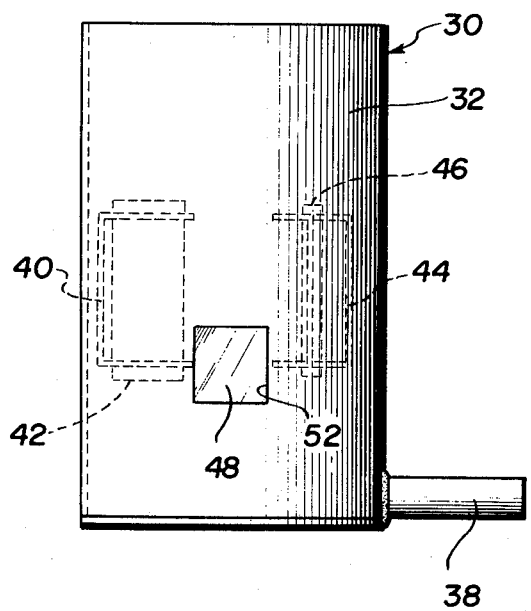
FIG. 2 is an enlarged elevational view of the sample container employed in the apparatus of FIG. 1.
Figure 3:
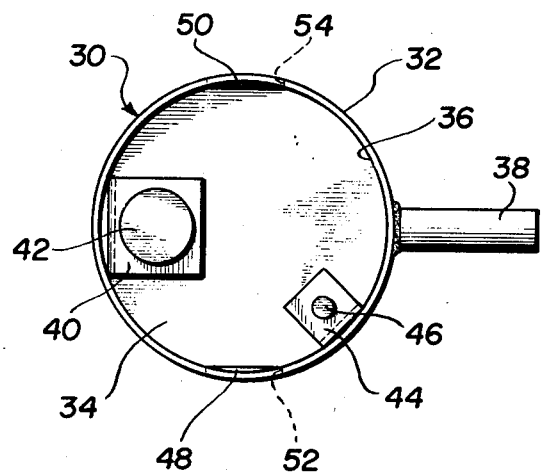
FIG. 3 is a top plan view of the sample container of FIG. 1.

Referring now to the drawings, and in particular to FIGS. 1–3, and apparatus for determining the pasting temperature of starch and the like is indicated generally at 10 in FIG. 1. The pasting temperature apparatus 10 includes a generally rectangularly shaped frame structure, indicated generally at 12, which includes end panels 14 and 16, top and bottom panels 18 and 20, respectively, and front and rear panels 22 and 24, respectively. The panels 14, 16, 18, 20, 22 and 24 making up the frame structure 12 of the pasting temperature device 10 may be made of any suitable material, such as sheet aluminum, and are secured together in a conventional manner. The top and front panels 18 and 22, respectively, are preferably detachable in a manner to allow their removal for access to the interior of the frame structure 12 to service the internal components.

A support pedestal 26 is secured to the upper surface of the bottom panel 20 within the frame structure 12 and supports a conventional magnetic stirrer 28. A container cup 30 is supported on the magnetic stirrer 28. With particular reference to FIGS. 2 and 3, the container cup 30 includes a cylindrical tubular body 32 which has a bottom plate 34 secured thereto to define an internal sample chamber 36 open at its upper end. The sample container cup 30 is adapted to receive a quantity of liquid, such as water, into which starch granules may be placed to form a starch slurry, as will be described more fully below. A drain tube 38 is connected to the tubular body 32 adjacent the lower end and has valve means (not shown) to allow selective draining of the contents of the chamber 36. In one embodiment of the pasting temperature determination apparatus 10, the sample container 30 was made from a two-inch nominal diameter tub approximately 3¼ inches long. The axial length of the pedestal 26 and the axial length of the magnetic stirrer body 28 are selected such that when the sample container 30 is supported on the magnetic stirrer, the upper end portion of the container 30 will extend upwardly through a suitable opening in the top panel 18 to provide access to the chamber 36 from outside the frame structure 12 for introducing water and starch granules into the chamber 36.

The magnetic stirrer 28 is of a known design and is operative to effect movement of a stirrer element (not shown) disposed within the chamber 36 of the sample chamber 30 to continuously stir the contents of the chamber 36. One type of magnetic stirrer which may be employed with the apparatus 10 is available from Fisher Scientific as Catalog No. 14-511-1V 2. The magnetic stirrer 28 is employed in an on-off mode controlled by a main power supply switch (not shown). The rate of stirring may generally be maintained constant as long as excessively viscoous materials are not employed.

A generally C-shaped heating element support bracket 40 is secured to the interior surface of the tubular body 32 of the sample container 30 upwardly from the bottom end 34 thereof, as shown in FIGS. 2 and 3. The support bracket 40 serves to releasably support a coventional immersion heater 42 which, in the illustrated embodiment, has a generally cylindrical configuration. The heating element 42 is connected to a suitable electric power supply (not shown) operative to selectively heat a starch slurry disposed within the chamber 36 of the container 30.

A second generally C-shaped bracket 44 is secured to the interior surface of the container cup body 32 at approximately the same distance from the bottom 34 of the container as the heater support bracket 40. The support bracket 44 is adapted to releasably support a thermistor probe 46 within the chamber 36. The thermistor probe 46 serves to measure the temperature of the starch slurry within the chamber 36 during heating by the immersion heater 32 and is connected to the input of a thermistor circuit module to be described more fully below. The thermistor circuit module is adapted to produce an output voltage which is precisely linear with the temperature detected by the thermistor probe 46. The thermistor probe 46 and associated thermistor circuit module 100 (shown in FIG. 4) are particularly desirable for use in the pasting temperature determination apparatus 10 because the thermistor output is compatible with a digital panel read-out meter. However, digital thermocouple temperature detecting units. compatible with digital panel meters may also be employed.

A pair of light-transparent windows 48 and 50 are sealingly secured within square apertures 52 and 54, respectively, formed in the tubular body 32 of the sample container 30. The square apertures 52 and 54 are spaced approximately one inch from the lower end 34 of the container 30 and are disposed in diametrically opposed relation angularly offset relative to the brackets 40 and 44.

Figure 4:
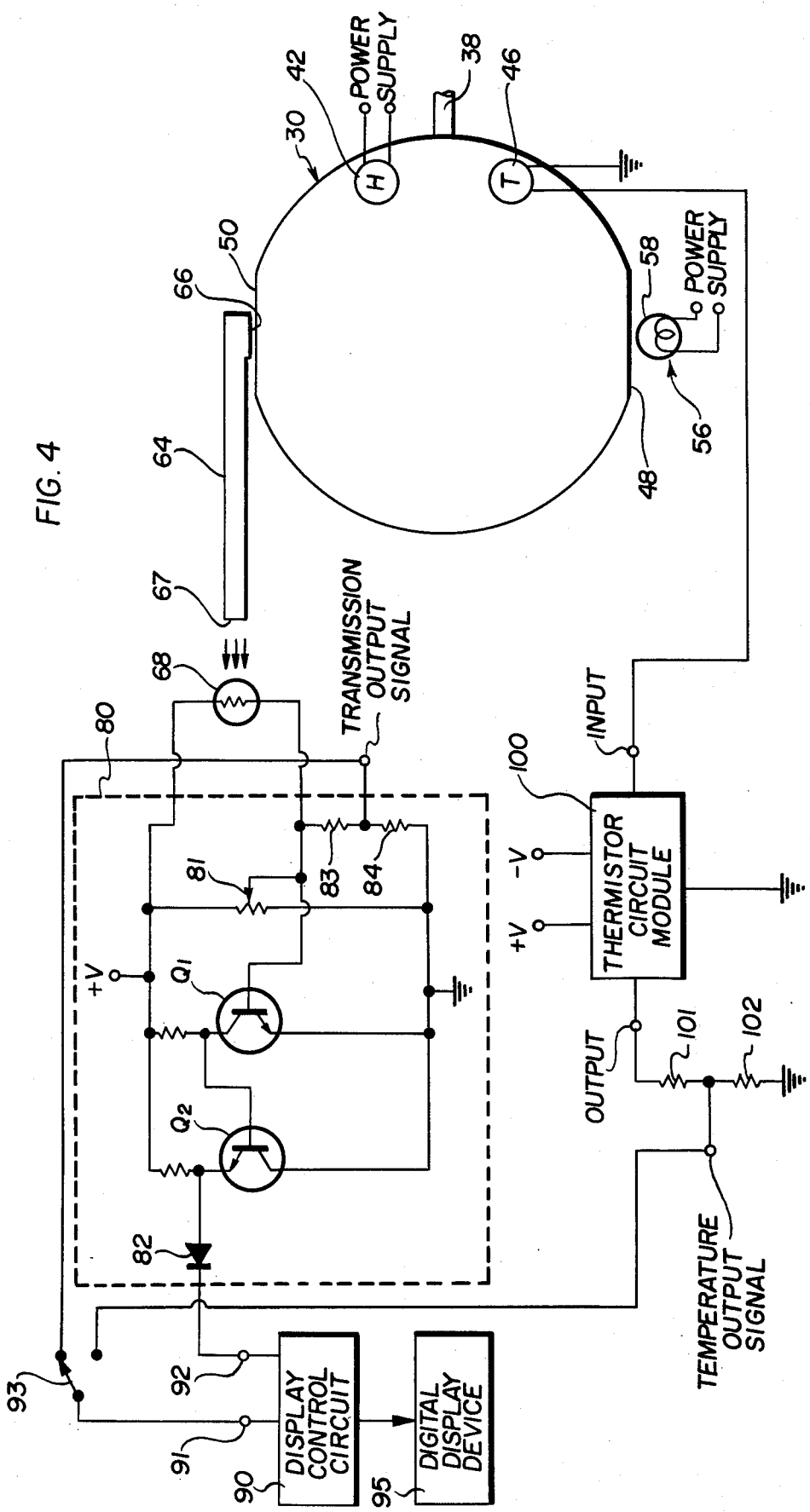
FIG. 4 is a schematic diagram of the sample container and associated circuitry in accordance with the present invention.

Considering FIG. 1, taken in conjunction with FIG. 4, a source of light, indicated generally at 56, is supported adjacent the outer surface of the optical window 48 and is adapted to transmit a light beam inwardly through the window 48 in alignment with the window 54. The source of light 56 may comprise a suitable incandescent lamp 58 operated in a conventional manner from a suitable power supply (not shown) and including, if desired, an on-off switch (not shown). The lamp 58 may be supported by a suitable support bracket 60 (FIG. 1) secured to the outer surface of the container cup body 32.

Any light transmitted through the optical window 48 and through the starch slurry sample disposed within the chamber 36 is detected through the optical window 50 by photosensor means, indicated generally at 62. The photosensor means 62 includes a conventional light conducting fiber optic tube 64 which has one end 66 disposed adjacent the optical windwo 50 to detect light passing through the chamber 36 from the light source 56. The fiber optic tube 64 has its other end 67 disposed adjacent a photocell 68 such that the photocell may detect light transmitted through optic tube 64. In this manner, the photocell 68 detects any light passing from the light source 58 through a slurry sample disposed within the chamber 36.

The light-transmission detector portion of the system shown in FIG. 4 includes the light source 56, the photocell 68, the light-conducting optical tube 64, and a solidstate switching circuit 80 coupled to the photocell 68. In general, when the lamp 58 of the light source 56 is energized, light emitted from the lamp which passes through tank 30 and the slurry contained therein is transmitted by the optical tube 64 to photocell 68 where it is converted into a corresponding electrical signal that is applied (through switch 93) to the signal input terminal 91 of a display control circuit 90.

The temperature detector portion of the system shown in FIG. 4 includes the thermistor 46 and the thermistor circuit module 100. In general, the temperature of the contents of the sample container 30 is detected by the thermistor whose output signal is amplified in module 100 to produce a signal that is applied (through the other terminal of switch 93) to the signal input terminal 91 of the display control circuit 90.

The control circuit 90 applies a suitable signal to a digital display device 95 to visually indicate the amount of light that is transmitted through the contents of sample container 30. The signal developed by photocell 68 is also used as a control signal to acutate switching circuit 80 when a predetermined threshold of light is detected, and serves to "hold" the display device 95 at a temperature reading corresponding to the predetermined light transmittance threshold.

The transmission of light through starch slurry varies of in accordance with the extent to which the starch granules have absorbed water and swollen. The initial swelling of starch granules in water dramatically affects the slurry's ability to block the transmission of light (opacity). While the starch is going through the transition from granular to pasted, the transmission increases at a rapid rate. The light intensity at the photocell eventually reaches a set threshold. For the embodiment of the invention illustrated in FIG. 4, the amount of light falling on the light-responsive portion of photocell 68 is directly related to the amount of light transmitted through the slurry sample in tank 30. Photocell 68 develops an electrical signal which varies in accordance with the amount of light falling on the photocell. By sensing the variations in the electrical signal of photocell 68, the condition, namely the transmittance, of the starch sample in container 30 can be determined rapidly and conveniently without disturbing the contents of the container.

Photocell 68 may comprise a conventional photoresistor (e.g. model CL904L manufactured by Clairex Electronics) as shown in FIG. 4 which has a resistance element whose resistance varies in a predetermined manner over a given range in accordance with the amount of light incident upon the light-responsive surface. By placing the photocell 68 in series with a power source (e.g. a positive 5 volt DC power supply, designated +V in FIG. 4, capable of supplying 1 amp. current while regulating the voltage ±0.5% during changes in load conditions) and connecting the photocell 68 to ground through another resistance (e.g., a voltage-divider resistance network consisting of suitable series-connected fixed resistors 83 and 84 shown in FIG. 4), an electrical signal in the form of a voltage is developed which has a variation in magnitude that corresponds to the amount of light incident upon the light-responsive portion of photocell 68. An output signal voltage is obtained between the resistors 83 and 84.

Switching circuit 80 includes a pair of switching transistors $Q_1$, and $Q_2$ (e.g. Sylvania transistors No. ECG 103), a suitable threshold-adjustment potentiometer 81, a diode 82 and the voltage-divider resistance network consisting of resistors 83 and 84. Potentiometer 81 is adjusted such that, when the amount of light incident upon the light-responsive portion of photocell 68 reaches a predetermined threshold level representative of the pasting temperature of the starch slurry in the container 30, the voltage applied to the base of switching transistor $Q_1$ is sufficient to render $Q_1$ conductive (e.g. "turn on"$Q_1$). The collector of $Q_1$ is connected to the base of switching transistor $Q_2$ so that, when switching transistor $Q_1$ is conducting, switching transistor $Q_2$ is turned off, i.e. non-conducting. When switching transistor $Q_2$ is nonconducting, its collector voltage is at its maximum, i.e. the level of +V. This voltage is applied to the "hold display" input 92 of the display control circuit 90 through a diode 82 to retain the displayed value indicated by the digital display device 95. The value displayed corresponds to the predetermined threshold amount of light transmitted through the slurry sample in the tank 30. As noted, this predetermined threshold of light transmission indicates that the starch slurry has reached its pasting temperature.

Display control circuit 90 and digital display device 95 may comprises any conventional display means capable of digitally displaying an analog signal and holding a predetermined display in response to the application of a suitable control signal (voltage). One such device that has been successfully employed is the Digital Panel Meter, Model No. AD 2003/DP, manufactured by Analog Devices. It converts an analog signal, ranging from 0 to 0.199 volts, to a 2½digit display and has a "hold display" input to retain a predetermined display in response to a suitable control signal.

Means for measuring and displaying the temperature of the slurry within the tank 30 are also provided in the embodiment of the invention illustrated in FIG. 4. This portion of the system includes the thermistor 46 mounted in the tank 30, and a thermistor circuit module 100 connected to the thermistor 46. Module 100 serves to amplify and condition the signal developed by the thermistor 46. The output of Module 100 is applied to the display control circuit 90 through a suitable voltage divider resistance network consisting of the series-connected fixed resistors. 101 and 102 and the selector switch 93. The values of resistors 101 and 102 are selected such that the voltage applied to the display control circuit 90 produces a display in display device 95 that directly indicates the temperature off the slurry within tank 30 in degrees Centigrade or Fahrenheit, etc. as desired. Thermistor 46 and thermistor circuit module 100 are conventional devices. Examples of such devices which have been used successfully in the illustrated embodiment of the invention are the thermistor conditioner module, Model No. 506, manufactured by Precision Digital Co., and a suitable thermistor probe is available from Yellow Springs Instrument Co., although other suitable thermistor devices may be utilized. The thermistor circuit module is connected to a ±15 volt DC power supply and is preferably calibrated to 1 volt D.C. per 100°C. with zero volts of 0°.

The selector switch 93 is provided at the signal input terminal 91 of display control circuit 90 to select either light transmission (output of the photocell 68) or temperature (output of thermistor module 100) for display by digital display device 95.

It can thus be seen that in accordance with the present invention, a pasting point detector apparatus is provided which utilizes the change in light transmission through a starch slurry during heating of the starch granules in water to determine the pasting temperature of the starch. Some starch modifications cause a change in pasting temperature of the starch. The difference in the pasting temperatures of a starch before and after reaction may be determined as representative of the extent of the reaction.

One method of operating the apparatus will be briefly described. The selector switch 93 is positioned to apply the signal from the light-transmission detector to the digital display device 95. The sample container cup 30 is assumed clean and its drain line 38 closed. The lamp 58 is turned on and allowed sufficient time to warm up. The sample container cup 30 is then filled with a measured volume of water, and the magnetic stirrer 28 is energized. If the starch sample which is to have its pasting temperature determined is dry, it is desirable that the dry starch granules be initially slurried some time (e.g. 2 hours) prior to introduction into the water within the container 30. This permits uniform hydration nof the granule and more reproducible determinations of pasting temperature. The starch sample need not be neutralized or specially washed; the impurities that normally are found in starch, such as inorganic salts do not interfere with the test.

The starch concentration in the sample container 30 is adjusted 4 times to provide four calibration values or readings on the digital display device 95 as follows.

With water in the sample cup, light transmission is at a high level, placing the output of switching circuit 80 at its maximum voltage so that display control circuit 90 is in hold condition. Sufficient starch slurry (1 to 5% solids) is added to the sample cup to reduce transmission and thereby the output voltage of photocell 68. This causes the switching circuit 80 to become nonconducting allowing the reading on display device 95 to change in response to applied voltage.

Next, the light transmittance reading is increased until there is no change in the reading on the display device when the instrument is switched to display temperature. This is the hold threshold value. This is accomplished first by adding water to the sample container sufficient to cause the light transmission display to increase by 0.1. Switch 93 is then actuated to cause the temperature (output of module 100) to be displayed. If the same, the reading is taken as the hold threshold value. If the reading is different, switch 93 is returned to the light-transmission position and water is again added to increase the displayed value by 0.1. Again, switch 93 is turned so that a reading of temperature is displayed. If the displayed reading is the same, this is taken as the hold threshold value. If not, the process is continued, switching to light transmission display, adding water and switching to temperature display until the readings are the same. At this point, light transmission through the starch slurry sample is just enough to cause the switching circuit to conduct and actuate the display control circuit to return to its hold condition.

Next, the starch concentration is adjusted to a predetermined level. This is accomplished by adding starch slurry to the sample, drop by drop. Initially, on addition of starch the switching circuit 80 is again returned to its non-conductive state, allowing the hold in the display control circuit 90 to be released. The addition of starch is continued to reduce the light-transmission display reading by a predetermined amount, for example 1.5 to 1.6 units below the hold threshold value. This determines the concentration of starch in the slurry sample, and can be called the "concentration" value.

The final step in preparing the sample is to adjust for variations in transmission that come about during the initial heating of the sample before pasting of the starch occurs. This adjustment is carried out while heat is being added to the sample. The switch 93 is placed in its "read-temperature" position so that the temperature is displayed on the display device 95. The heating element 42 is energized from its power supply. The slurry is heated toward the pasting temperature of the starch. After the slurry temperature has risen to some chosen value, say 20°C. below the expected pasting temperature, the switch 93 is moved to its "read-transmission" setting. The reading should be 1.0 to 1.1 units below the "hold threshold value". If the transmittance reading is too high, additional slurry is quickly added to reduce the reading; if the reading is too low, water is added to raise it to 1.0 to 1.1 units below the hold threshold value. For most starch products, this has to be accomplished before the temperature reaches 50°C. If more time is required to make the adjustment, the heater 42 can be turned off until the adjustment is completed. At 50°C., the transmission reading should be steady at 1.0 to 1.1 units below the hold threshold value for 20 seconds; if it is not, the concentration should be adjusted further until it is steady at the desired value for 20 seconds or so.

After the final adjustment, heating of the starch slurry is resumed or continued and switch 93 moved to its read-temperature position so that display device 95 shows temperature. As the starch is heated toward its pasting temperature. the granules hydrate and lose opacity. This increases the light transmission through the sample container 30, increasing the incident light on photocell 68. With the increasing light on the photocell, its output voltage rises until the holdthreshold voltage is obtained and switching circuit 80 is actuated. Simultaneously the temperature signal voltage from thermistor 46 has been applied by thermistor module 100 through switch 93 and display control circuit 90 to the display device. When the switching circuit 80 is actuated at the point of rapid rise of light transmission, the temperature reading on the display device 95 is fixed and remains constant, even though the temperature of the sample continues to rise. This reading is taken as the pasting temperature.

The heater is turned off, and the sample cup is then drained and cleaned by filling the cup with water and allowing it to drain completely three times.

A differential pasting temperature of a modified starch is calculated by substracting the pasting temperature of the starting unmodified starch from the pasting temperature of the product as shown by the temperature reading on the display device 95 following the above set forth method.

With the apparatus 10 calibrated as aforedescribed, the pasting temperatures of starch samples may be determined more quickly as follows. The main power supply is turned on and the selector switch 93 is switch to a position to display the light transmission. Water (e.g. about 110 milliliters) is added to the sample cup 30 (e.g. to about one inch from the top of the cup. Starch granules suspended in water are then added to the water within the container cup 30 until the digital display device 95 displays a reading in the concentration value range (1.5–1.6 units below the hold threshold value). The switch 93 is then placed in its read-temperature position so that display device 95 provides a reading of the temperature of the slurry within the container cup. The heating element 42 is then energized. At 42°C., the transmission is adjusted as described above to take into account transmission change during heating but before pasting. Then the temperature is displayed and heating continued. When the pasting temperature of the starch within the container cup is reached, the display device 95 is automatically locked in hold condition and indicates the pasting temperature. The slurry sample is thereafter drained from the container cup 30 and the sample cup is rinsed preparatory to testing a subsequent starch sample.

While a preferred embodiment of the present invention has been illustrated and described, it will be obvious to those skilled in the art that changes and modifications may be made therein without departing from the invention in its broader aspects. For example, any magnetic or mechanical stirrer may be employed; a beaker may be utilized in place of the sample container cup 30; any immersion heater having a heaing capacity up to 120 watts may be employed; and alternate optical filters, polarizers, and alternate light sources may be employed. Various features of the invention are defined in the following claims.

What is claimed is:

1. The method of determining the pasting temperature of starch and the like, comprising the steps of mixing a predetermined quantity of starch sample into a predetermined quantity of water to form a starch slurry, heating said slurry, continuously monitoring the temperature of said slurry as it is heated, directing a light beam in a direction through said starch slurry while heating said slurry, detecting the light passed through said slurry by said light beam and creating a signal proportional to the amount of light detected, transmitting said signal to a display device and displaying the light transmissivity through said slurry on said display device, placing said display device in a hold condition when transmissivity of light through said slurry reaches a predetermined threshold representative of the pasting temperature of the starch, and causing said display device to display the temperature of said slurry during said hold condition when said predetermined light threshold is reached.

2. The method as defined in claim 1 including the step of stirring said slurry during heating thereof.

3. The method as defined in claim 1 including the step of transmitting a signal to said display device in a manner to automatically place said device in said hold condition when the light detected passing through said slurry reaches said predetermined light threshold.

4. A method for determining the temperature at which the granules of a cloudy two-phase substantially opaque liquid slurry start to swell and form a light transmitting single-phase mixture, comprising the steps of placing a predetermined quantity of an opaque two-phase liquid slurry mixture into a container, heating the mixture to increase the temperature thereof from a generally atmospheric temperature through a temperature range which includes the probable temperature of the mixture at which the granules start to swell and become light transmitting, subjecting the mixture to a light beam in a direction through the mixture while being heated, continually detecting the extent of light passage through said mixture and creating a first signal proportional to the light transmitted through said slurry, monitoring the temperature of the mixture as said mixture is being heated and creating a second signal proportional to the temperature of said slurry, transmitting said first signal to a display device and displaying a visual reading on said display device which represents the light transmissivity through said mixture, placing said visual display device in a hold condition when a predetermined threshold of light is transmitted through said mixture during heating thereof, said threshold being the point at which the granules of slurry being to swell, and transmitting said second signal to said display device and causing said display device to indicate the temperature of said mixture when said display device is placed in said hold condition.

* * * * *

UNITED STATES PATENT AND TRADEMARK OFFICE
CERTIFICATE OF CORRECTION

PATENT NO. : 3,982,420
DATED : September 28, 1976
INVENTOR(S) : Charles W. Blevins and Thomas F. Protzman It is certified that error appears in the above-identified patent and that said Letters Patent are hereby corrected as shown below:

```
Col. 3, line  4, change "tub" to --tube--;
Col. 4, line 15, change "windwo" to --window--;
Col. 5, line 48, change "comprises" to --comprise--;
Col. 6, line 45, change "nof" to --of--;
Col. 6, line 56, "hold" should be in quotations;
Col. 7, line 15, "hold" should be in quotations;
Col. 7, line 40, "hold threshold" should be in quotations;
Col. 7, line 49, "hold threshold" should be in quotations;
Col. 7, line 55, "read temperature" should be in quotations;
Col. 8, line 22, "concentration" should be in quotations;
Col. 8, line 24, "hold threshold" should be in quotations;

Col. 10, line 16, change "being" to --begin--.
```

Signed and Sealed this

Fifth Day of April 1977

[SEAL]

Attest:

RUTH C. MASON
Attesting Officer

C. MARSHALL DANN
Commissioner of Patents and Trademarks